United States Patent [19]
Stewart

[11] Patent Number: 5,604,686
[45] Date of Patent: Feb. 18, 1997

[54] METHOD AND APPARATUS FOR ANALYZING CHEMICAL SYSTEMS

[75] Inventor: James J. P. Stewart, Colorado Springs, Colo.

[73] Assignee: Fujitsu, Ltd., Kawasaki, Japan

[21] Appl. No.: 92,687

[22] Filed: Jul. 16, 1993

[51] Int. Cl.⁶ .................................................. G06F 17/50
[52] U.S. Cl. ............................................ 364/578; 364/496
[58] Field of Search ..................................... 364/578, 499, 364/496, 497, 498

[56] References Cited

PUBLICATIONS

P. W. Atkins, *Physical Chemistry*, Third Edition (1986).
MOPAC 93, Fujitsu Limited, First Edition, May 1993.

*Primary Examiner*—Ellis B. Ramirez
*Assistant Examiner*—Eric W. Stamber
*Attorney, Agent, or Firm*—Staas & Halsey

[57] ABSTRACT

A method and apparatus analyze chemical compounds from molecular geometric data of a chemical compound. Localized molecular orbitals are used to form a density matrix and a Fock matrix. The method and apparatus performs an annihilation process on the Fock matrix to interactively eliminate the interaction of each bonding orbital with each non-bonding orbital, i.e., $\psi F \psi^*$, where $\psi$ is a bonding orbital, F is a corresponding member of the Fock matrix and $\psi^*$ is an antibonding orbital. The annihilation process involves a simple diagonalization of a 2×2 matrix and replaces the very lengthy calculation of diagonalizing the Fock matrix, as is done in the related art. To further speed up the process, the method and apparatus of the present invention determine which of the bonding orbitals and antibonding orbitals cannot interact using interatomic distances. The interaction for these bonding orbitals and antibonding orbitals is not eliminated in the annihilation process. The apparatus of the present invention includes at least one input means, processing means, output device and means for generating a control specification.

2 Claims, 29 Drawing Sheets

FIG. 5

| ATOM NUMBER (I) | CHEMICAL SYMBOL | BOND LENGTH (ANGSTROMS) NA:I | BOND ANGLE (DEGREES) NB:NA:I | TWIST ANGLE (DEGREES) NC:NB:NA:I | NA | NB | NC |
|---|---|---|---|---|---|---|---|
| 1 | H | | | | | | |
| 2 | H | 0.70000 | | | 1 | | |
| 3 | H | 1.60000 | 180.00000 | | 2 | 1 | |
| 4 | H | 0.70000 | 180.00000 | 0.00000 | 3 | 2 | 1 |
| 5 | H | 1.60000 | 180.00000 | 0.00000 | 4 | 3 | 2 |
| 6 | H | 0.70000 | 180.00000 | 0.00000 | 5 | 4 | 3 |
| 7 | H | 1.60000 | 180.00000 | 0.00000 | 6 | 5 | 4 |
| 8 | H | 0.70000 | 180.00000 | 0.00000 | 7 | 6 | 5 |
| 9 | H | 1.60000 | 180.00000 | 0.00000 | 8 | 7 | 6 |
| 10 | H | 0.70000 | 180.00000 | 0.00000 | 9 | 8 | 7 |
| 11 | H | 1.60000 | 180.00000 | 0.00000 | 10 | 9 | 8 |
| 12 | H | 0.70000 | 180.00000 | 0.00000 | 11 | 10 | 9 |

FIG. 6

| NO. | ATOM | X | Y | Z |
|-----|------|--------|--------|--------|
| 1 | H | 0.0000 | 0.0000 | 0.0000 |
| 2 | H | 0.7000 | 0.0000 | 0.0000 |
| 3 | H | 1.7000 | 0.0000 | 0.0000 |
| 4 | H | 2.4000 | 0.0000 | 0.0000 |
| 5 | H | 3.4000 | 0.0000 | 0.0000 |
| 6 | H | 4.1000 | 0.0000 | 0.0000 |
| 7 | H | 5.1000 | 0.0000 | 0.0000 |
| 8 | H | 5.8000 | 0.0000 | 0.0000 |
| 9 | H | 6.8000 | 0.0000 | 0.0000 |
| 10 | H | 7.5000 | 0.0000 | 0.0000 |
| 11 | H | 8.5000 | 0.0000 | 0.0000 |
| 12 | H | 9.2000 | 0.0000 | 0.0000 |

FIG. 7A

ONE-ELECTRON MATRIX FROM HCORE

|   |   | H1 | H2 | H3 | H4 | H5 | H6 |
|---|---|---|---|---|---|---|---|
| H | 1 | -55.138448 | | | | | |
| H | 2 | -4.556495 | -62.257049 | | | | |
| H | 3 | -1.102314 | -3.174686 | -68.563757 | | | |
| H | 4 | -0.319372 | -1.102314 | -4.556495 | -71.258280 | | |
| H | 5 | -0.045587 | -0.181244 | -1.102314 | -3.174686 | -73.523467 | |
| H | 6 | -0.010789 | -0.045587 | -0.319372 | -1.102314 | -4.556495 | -74.257243 |
| H | 7 | -0.001279 | -0.005735 | -0.045587 | -0.181244 | -1.102314 | -3.174686 |
| H | 8 | -0.000277 | -0.001279 | -0.010789 | -0.045587 | -0.319372 | -1.102314 |
| H | 9 | -0.000030 | -0.000142 | -0.001279 | -0.005735 | -0.045587 | -0.181244 |
| H | 10 | -0.000006 | -0.000030 | -0.000277 | -0.001279 | -0.010789 | -0.045587 |
| H | 11 | -0.000001 | -0.000003 | -0.000030 | -0.000142 | -0.001279 | -0.005735 |
| H | 12 | 0.000000 | -0.000001 | -0.000006 | -0.000030 | -0.000277 | -0.001279 |

FIG. 7B

ONE-ELECTRON MATRIX FROM HCORE

| O | | H7 | H8 | H9 | H10 | H11 | H12 |
|---|---|---|---|---|---|---|---|
| H | 7 | -74.257243 | | | | | |
| H | 8 | -4.556495 | -73.523467 | | | | |
| H | 9 | -1.102314 | -3.174686 | -71.258280 | | | |
| H | 10 | -0.319372 | -1.102314 | -4.556495 | -68.563757 | | |
| H | 11 | -0.045587 | -0.181244 | -1.102314 | -3.174686 | -62.257049 | |
| H | 12 | -0.010789 | -0.045587 | -0.319372 | -1.102314 | -4.556495 | -55.138448 |

FIG. 8

TWO-ELECTRON INTEGRALS IN HCORE

| 10.8972 | 7.0718 | 9.5867 | 5.4363 | 7.0718 | 10.8972 | 4.0223 | 4.9257 | 7.0718 | 9.5867 |
|---|---|---|---|---|---|---|---|---|---|
| 3.3878 | 4.0223 | 5.4363 | 7.0718 | 10.8972 | 2.7577 | 3.1714 | 4.0223 | 4.9257 | 7.0718 |
| 9.5867 | 2.4376 | 2.7577 | 3.3878 | 4.0223 | 5.4363 | 7.0718 | 10.8972 | 2.0894 | 2.3217 |
| 2.7577 | 3.1714 | 4.0223 | 4.9257 | 7.0178 | 9.5867 | 1.8989 | 2.0894 | 2.4376 | 2.7577 |
| 3.3878 | 4.0223 | 5.4363 | 7.0718 | 10.8972 | 1.6795 | 1.8273 | 2.0894 | 2.3217 | 2.7577 |
| 3.1714 | 4.0223 | 4.9257 | 7.0718 | 9.5867 | 1.5537 | 1.6795 | 1.8989 | 2.0894 | 2.4376 |
| 2.7577 | 3.3878 | 4.0223 | 5.4363 | 7.0718 | 10.8972 | | | | |

FIG. 9

LOCALIZED FILLED M.O.s

| M.O. No. 1 | 0.7071 1 | 0.7071 2 | 0.0000 3 | 0.0000 4 | 0.0000 5 | 0.0000 6 | 0.0000 7 | 0.0000 8 | 0.0000 9 | 0.0000 10 |
|---|---|---|---|---|---|---|---|---|---|---|
| M.O. No. 2 | 0.7071 3 | 0.7071 4 | 0.0000 1 | 0.0000 2 | 0.0000 5 | 0.0000 6 | 0.0000 7 | 0.0000 8 | 0.0000 9 | 0.0000 10 |
| M.O. No. 3 | 0.7071 5 | 0.7071 6 | 0.0000 1 | 0.0000 2 | 0.0000 3 | 0.0000 4 | 0.0000 7 | 0.0000 8 | 0.0000 9 | 0.0000 10 |
| M.O. No. 4 | 0.7071 7 | 0.7071 8 | 0.0000 1 | 0.0000 2 | 0.0000 3 | 0.0000 4 | 0.0000 5 | 0.0000 6 | 0.0000 9 | 0.0000 10 |
| M.O. No. 5 | 0.7071 9 | 0.7071 10 | 0.0000 1 | 0.0000 2 | 0.0000 3 | 0.0000 4 | 0.0000 5 | 0.0000 6 | 0.0000 7 | 0.0000 8 |
| M.O. No. 6 | 0.7071 11 | 0.7071 12 | 0.0000 1 | 0.0000 2 | 0.0000 3 | 0.0000 4 | 0.0000 5 | 0.0000 6 | 0.0000 7 | 0.0000 8 |

FIG. 10A

DENSITY MATRIX ON ITERATION 0

|   | H1 | H2 | H3 | H4 | H5 | H6 |
|---|---|---|---|---|---|---|
| H 1 | 1.000000 | | | | | |
| H 2 | 1.000000 | 1.000000 | | | | |
| H 3 | 0.000000 | 0.000000 | 1.000000 | | | |
| H 4 | 0.000000 | 0.000000 | 1.000000 | 1.000000 | | |
| H 5 | 0.000000 | 0.000000 | 0.000000 | 0.000000 | 1.000000 | |
| H 6 | 0.000000 | 0.000000 | 0.000000 | 0.000000 | 1.000000 | 1.000000 |
| H 7 | 0.000000 | 0.000000 | 0.000000 | 0.000000 | 0.000000 | 0.000000 |
| H 8 | 0.000000 | 0.000000 | 0.000000 | 0.000000 | 0.000000 | 0.000000 |
| H 9 | 0.000000 | 0.000000 | 0.000000 | 0.000000 | 0.000000 | 0.000000 |
| H 10 | 0.000000 | 0.000000 | 0.000000 | 0.000000 | 0.000000 | 0.000000 |
| H 11 | 0.000000 | 0.000000 | 0.000000 | 0.000000 | 0.000000 | 0.000000 |
| H 12 | 0.000000 | 0.000000 | 0.000000 | 0.000000 | 0.000000 | 0.000000 |

FIG. 10B

DENSITY MATRIX ON ITERATION 0

| | H 7 | H 8 | H 9 | H 10 | H 11 | H 12 |
|---|---|---|---|---|---|---|
| H 7 | 1.000000 | | | | | |
| H 8 | 1.000000 | 1.000000 | | | | |
| H 9 | 0.000000 | 0.000000 | 1.000000 | | | |
| H 10 | 0.000000 | 0.000000 | 1.000000 | 1.000000 | | |
| H 11 | 0.000000 | 0.000000 | 0.000000 | 0.000000 | 1.000000 | |
| H 12 | 0.000000 | 0.000000 | 0.000000 | 0.000000 | 1.000000 | 1.000000 |

FIG. 11A

FOCK MATRIX ON ITERATION 0

|    | H1         | H2         | H3         | H4         | H5         | H6         |
|----|------------|------------|------------|------------|------------|------------|
| H 1  | -5.482276  |            |            |            |            |            |
| H 2  | -10.005087 | -5.482276  |            |            |            |            |
| H 3  | -0.384168  | -1.299651  | -5.482276  |            |            |            |
| H 4  | -0.101213  | -0.384168  | -10.005087 | -5.482276  |            |            |
| H 5  | -0.003748  | -0.016368  | -0.384168  | -1.299651  | -5.482276  |            |
| H 6  | -0.000828  | -0.003748  | -0.101213  | -0.384168  | -10.005087 | -5.482276  |
| H 7  | -0.000024  | -0.000114  | -0.003748  | -0.016368  | -0.384168  | -1.299651  |
| H 8  | -0.000005  | -0.000024  | -0.000828  | -0.003748  | -0.101213  | -0.384168  |
| H 9  | -0.000000  | -0.000001  | -0.000024  | -0.000114  | -0.003748  | -0.016368  |
| H 10 | 0.000000   | 0.000000   | -0.000005  | -0.000024  | -0.000828  | -0.003748  |
| H 11 | 0.000000   | 0.000000   | 0.000000   | -0.000001  | -0.000024  | -0.000114  |
| H 12 | 0.000000   | 0.000000   | 0.000000   | 0.000000   | -0.000005  | -0.000024  |

FIG. 11B

FOCK MATRIX ON ITERATION 0

|    | H7        | H8        | H9        | H10       | H11       | H12       |
|----|-----------|-----------|-----------|-----------|-----------|-----------|
| H7 | -5.482276 |           |           |           |           |           |
| H8 | -10.005087| -5.482276 |           |           |           |           |
| H9 | -0.384168 | -1.299651 | -5.482276 |           |           |           |
| H10| -0.101213 | -0.384168 | -10.005087| -5.482276 |           |           |
| H11| -0.003748 | -0.016368 | -0.384168 | -1.299651 | -5.482276 |           |
| H12| -0.000828 | -0.003748 | -0.101213 | -0.384168 | -10.005087| -5.482276 |

FIG. 12

LOCALIZED FILLED M.O.s

| M.O. No. | 1 | 2 | 3 | 4 | 5 | 6 | 7 | 8 | 9 | 10 | 11 | 12 |
|---|---|---|---|---|---|---|---|---|---|---|---|---|
| 1 | 0.7086 | 0.7068 | 0.0211 | -0.0211 | 0.0000 | 0.0000 | 0.0000 | 0.0000 | 0.0000 | 0.0000 | | |
| 2 | | | | | | | | | | | | |
| 2 | 0.7065 | 0.7065 | -0.0211 | 0.0211 | 0.0211 | -0.0211 | 0.0000 | 0.0000 | 0.0000 | 0.0000 | | |
| 3 | | | | | | | | | | | | |
| 3 | 0.7065 | 0.7065 | 0.0006 | 0.0006 | -0.0211 | 0.0211 | 0.0211 | -0.0211 | 0.0000 | 0.0000 | | |
| 5 | | | | | | | | | | | | |
| 4 | 0.7065 | 0.7065 | 0.0000 | 0.0000 | 0.0006 | 0.0006 | -0.0211 | 0.0211 | 0.0211 | -0.0211 | | |
| 7 | | | | | | | | | | | | |
| 5 | 0.7065 | 0.7065 | 0.0000 | 0.0000 | 0.0000 | 0.0000 | 0.0006 | -0.0006 | -0.0211 | 0.0211 | | |
| 9 | | | | | | | | | | | | |
| 6 | 0.7068 | 0.7068 | 0.0000 | 0.0000 | 0.0000 | 0.0000 | 0.0000 | 0.0006 | 0.0006 | 0.0006 | | |
| 11 | | | | | | | | | | | | |

FIG. 13A

DENSITY MATRIX ON ITERATION 1

|   | H1 | H2 | H3 | H4 | H5 | H6 |
|---|---|---|---|---|---|---|
| O |  |  |  |  |  |  |
| H 1 | 1.000000 |  |  |  |  |  |
| H 2 | 0.998213 | 1.000000 |  |  |  |  |
| H 3 | 0.000000 | 0.059731 | 1.000000 |  |  |  |
| H 4 | -0.059731 | 0.000000 | 0.996426 | 1.000000 |  |  |
| H 5 | 0.000000 | 0.001786 | 0.000000 | 0.059704 | 1.000000 |  |
| H 6 | 0.001786 | 0.000000 | -0.059704 | 0.000000 | 0.996426 | 1.000000 |
| H 7 | 0.000000 | 0.000053 | 0.000000 | 0.001785 | 0.000000 | 0.059704 |
| H 8 | 0.000053 | 0.000000 | 0.001785 | 0.000000 | -0.059704 | 0.000000 |
| H 9 | 0.000000 | 0.000002 | 0.000000 | 0.000053 | 0.000000 | 0.001785 |
| H 10 | -0.000053 | 0.000000 | -0.000053 | 0.000000 | 0.001785 | 0.000000 |
| H 11 | 0.000000 | 0.000000 | 0.000000 | 0.000002 | 0.000000 | 0.000053 |
| H 12 | 0.000002 | 0.000000 | 0.000002 | 0.000000 | -0.000053 | 0.000000 |

FIG. 13B

DENSITY MATRIX ON ITERATION 1

|   | H7 | H8 | H9 | H10 | H11 | H12 |
|---|---|---|---|---|---|---|
| H 7 | 1.000000 | | | | | |
| H 8 | 0.996426 | 1.000000 | | | | |
| H 9 | 0.000000 | 0.059704 | 1.000000 | | | |
| H 10 | -0.059604 | 0.000000 | 0.996424 | 1.000000 | | |
| H 11 | 0.000000 | 0.001787 | 0.000000 | 0.059758 | 1.000000 | |
| H 12 | 0.001787 | 0.000000 | -0.059758 | 0.000000 | 0.998211 | 1.000000 |

FIG. 14A

FOCK MATRIX ON ITERATION 1

|   | H1 | H2 | H3 | H4 | H5 | H6 |
|---|---|---|---|---|---|---|
| H 1 | -5.482276 | -5.482276 | -5.482276 | -5.482276 | -5.482276 | -5.482276 |
| H 2 | -9.995350 | -1.519797 | -9.985613 | -1.519698 | -9.985613 | -1.519698 |
| H 3 | -0.384168 | -0.384168 | -0.384168 | -0.384168 | -0.384168 | -0.384168 |
| H 4 | -0.033072 | -0.019538 | -0.033012 | -0.019536 | 0.033012 | -0.019536 |
| H 5 | -0.003748 | -0.003748 | -0.003748 | -0.003748 | -0.003748 | -0.003748 |
| H 6 | -0.003202 | -0.003202 | -0.003201 | -0.000175 | -0.003201 | -0.000175 |
| H 7 | -0.000024 | -0.000024 | -0.000024 | -0.000024 | -0.000024 | -0.000024 |
| H 8 | 0.000045 | -0.000002 | 0.000045 | -0.000002 | 0.000045 | -0.000002 |
| H 9 | 0.000000 | -0.000000 | 0.000000 | 0.000000 | 0.000000 | 0.000000 |
| H 10 | -0.000001 | 0.000000 | -0.000001 | 0.000000 | 0.000000 | 0.000000 |
| H 11 | 0.000000 | 0.000000 | 0.000000 | 0.000000 | 0.000000 | 0.000000 |
| H 12 | 0.000000 | 0.000000 | 0.000000 | 0.000000 | 0.000000 | 0.000000 |

ITERATION 1 PLS = 0.100E+01 0.99E+00 ENERGY 33.6714998 DELTAE -10.7107041

FIG. 14B

FOCK MATRIX ON ITERATION 1

|   | H7 | H8 | H9 | H10 | H11 | H12 |
|---|---|---|---|---|---|---|
| O |  |  |  |  |  |  |
| H 7 | -5.482276 |  |  |  |  |  |
| H 8 | -9.985613 | -5.482276 |  |  |  |  |
| H 9 | -0.384168 | -1.519698 | -5.482276 |  |  |  |
| H 10 | 0.033012 | -0.384168 | -9.985604 | -5.482276 |  |  |
| H 11 | -0.003748 | -0.019539 | -0.384168 | -1.519895 | -5.482276 |  |
| H 12 | -0.003203 | -0.003748 | 0.033132 | -0.384168 | -9.995341 | -5.482276 |

ITERATION 1 PLS = 0.100E+01 099E+00 ENERGY 33.6714998 DELTAE -10.7107041

FIG. 15A

DENSITY MATRIX ON ITERATION 11

|   | H 1 | H 2 | H 3 | H 4 | H 5 | H 6 |
|---|---|---|---|---|---|---|
| H 1 | 1.005996 | | | | | |
| H 2 | 0.996313 | 0.994079 | | | | |
| H 3 | -0.000195 | 0.085528 | 1.000363 | | | |
| H 4 | -0.084948 | 0.000667 | 0.992678 | 0.999573 | | |
| H 5 | 0.000011 | -0.003055 | -0.000040 | 0.085817 | 1.000065 | |
| H 6 | 0.010292 | -0.000083 | -0.084667 | 0.000073 | 0.992649 | 0.999925 |
| H 7 | -0.000001 | 0.000223 | 0.000001 | -0.003084 | 0.000007 | 0.085817 |
| H 8 | -0.001361 | 0.000012 | 0.010266 | -0.000009 | -0.084660 | 0.000007 |
| H 9 | 0.000000 | -0.000021 | 0.000001 | -0.000228 | -0.000009 | -0.003084 |
| H 10 | 0.000188 | -0.000001 | -0.001360 | 0.000001 | 0.010266 | 0.000001 |
| H 11 | 0.000000 | 0.000001 | -0.000001 | 0.000021 | 0.000012 | 0.000223 |
| H 12 | -0.000026 | 0.000000 | 0.000188 | 0.000000 | -0.001361 | -0.000001 |

FIG. 15B

DENSITY MATRIX ON ITERATION 11

|   | H7 | H8 | H9 | H10 | H11 | H12 |
|---|---|---|---|---|---|---|
| H7  | 0.999925 |  |  |  |  |  |
| H8  | 0.992649 | 1.000065 |  |  |  |  |
| H9  | 0.000073 | 0.085817 | 0.999573 |  |  |  |
| H10 | -0.084667 | -0.000040 | 0.992678 | 1.000363 |  |  |
| H11 | -0.000083 | -0.003055 | 0.000667 | 0.085528 | 0.994079 |  |
| H12 | 0.010292 | 0.000011 | -0.084948 | -0.000195 | 0.996313 | 1.005996 |

FIG. 16A

FOCK MATRIX ON ITERATION 11

|   |    | H1         | H2        | H3        | H4        | H5        | H6        |
|---|----|------------|-----------|-----------|-----------|-----------|-----------|
| H | 1  | -5.508669  |           |           |           |           |           |
| H | 2  | -9.984999  | -5.455278 |           |           |           |           |
| H | 3  | -0.383619  | -1.614876 | -5.495264 |           |           |           |
| H | 4  | 0.089765   | -0.386045 | -9.965191 | -5.488304 |           |           |
| H | 5  | -0.003766  | -0.010948 | -0.384056 | -1.615941 | -5.487986 |           |
| H | 6  | -0.014506  | -0.003623 | 0.089132  | -0.384374 | -9.965033 | -5.486677 |
| H | 7  | -0.000023  | -0.000369 | -0.003749 | -0.010897 | -0.384187 | -1.615941 |
| H | 8  | 0.001271   | -0.000036 | -0.014473 | -0.003735 | 0.089117  | -0.384187 |
| H | 9  | 0.000000   | 0.000017  | -0.000025 | -0.000374 | -0.003735 | -0.010897 |
| H | 10 | -0.000136  | 0.000001  | 0.001270  | -0.000025 | -0.014473 | -0.003749 |
| H | 11 | 0.000000   | -0.000001 | 0.000001  | 0.000017  | -0.000036 | -0.000369 |
| H | 12 | 0.000015   | 0.000000  | -0.000136 | 0.000000  | 0.001271  | -0.000023 |

FIG. 16B

FOCK MATRIX ON ITERATION 11

|   | H 7 | H 8 | H 9 | H 10 | H 11 | H 12 |
|---|---|---|---|---|---|---|
| H 7 | -5.486677 | | | | | |
| H 8 | -9.965033 | -5.487986 | | | | |
| H 9 | -0.384374 | -1.615941 | -5.488304 | | | |
| H 10 | 0.089132 | -0.384056 | -9.965191 | -5.495264 | | |
| H 11 | -0.003623 | -0.010948 | -0.386045 | -1.614876 | -5.455278 | |
| H 12 | -0.014506 | -0.003766 | 0.089765 | -0.383619 | -9.984999 | -5.508669 |

FIG. 17

LOCALIZED FILLED M.O.s

| M.O. | | | | | | | | | | |
|---|---|---|---|---|---|---|---|---|---|---|
| M.O. No. 1 | 0.7086 / 1 | 0.7044 / 2 | 0.0302 / 3 | -0.0299 / 4 | -0.0021 / 5 | 0.0026 / 6 | 0.0002 / 7 | -0.0003 / 8 | 0.0000 / 9 | 0.0000 / 10 |
| M.O. No. 2 | 0.7059 / 3 | 0.7057 / 4 | -0.0303 / 1 | 0.0304 / 2 | 0.0303 / 5 | -0.0301 / 6 | -0.0021 / 7 | 0.0027 / 8 | 0.0002 / 9 | -0.0003 / 10 |
| M.O. No. 3 | 0.7058 / 5 | 0.7058 / 6 | 0.0034 / 1 | -0.0014 / 2 | -0.0301 / 3 | 0.0303 / 4 | 0.0303 / 7 | -0.0301 / 8 | -0.0021 / 9 | 0.0027 / 10 |
| M.O. No. 4 | 0.7058 / 7 | 0.7058 / 8 | -0.0004 / 1 | 0.0002 / 2 | 0.0034 / 3 | -0.0014 / 4 | -0.0301 / 5 | 0.0303 / 6 | 0.0303 / 9 | -0.0302 / 10 |
| M.O. No. 5 | 0.7057 / 9 | 0.7059 / 10 | 0.0000 / 1 | 0.0000 / 2 | -0.0004 / 3 | 0.0002 / 4 | 0.0034 / 5 | -0.0014 / 6 | -0.0301 / 7 | 0.0303 / 8 |
| M.O. No. 6 | 0.7044 / 11 | 0.7086 / 12 | 0.0000 / 1 | 0.0000 / 3 | 0.0000 / 4 | -0.0004 / 5 | 0.0002 / 6 | 0.0033 / 7 | -0.0014 / 8 | -0.0298 / 9 |

FIG. 18

GEO-OK SIZES DEBUG DENSITY FOCK ITER PL 1SCF  PRECISE
H6 (Chain)

1SCF WAS SPECIFIED, SO BFGS WAS NOT USED
SCF FIELD WAS ACHIEVED

MNDO    CALCULATION

VERSION 95.00
Sun Jul 11 10:11:47 1993

FINAL HEAT OF FORMATION = 32.57287 KCAL = 136.28487 KJ

NO. OF FILLED LEVELS = 6
MOLECULAR WEIGHT = 12.095

SCF CALCULATIONS = 1
COMPUTATION TIME = 0.790 SECONDS

FIG. 19

| ATOM NUMBER (I) | CHEMICAL SYMBOL | BOND LENGTH (ANGSTROMS) NA:I | BOND ANGLE (DEGREES) NB:NA:I | TWIST ANGLE (DEGREES) NC:NB:NA:I | NA | NB | NC |
|---|---|---|---|---|---|---|---|
| 1 | H | | | | | | |
| 2 | H | 0.70000 | | | 1 | | |
| 3 | H | 1.60000 | 180.00000 | | 2 | 1 | |
| 4 | H | 0.70000 | 180.00000 | 0.00000 | 3 | 2 | 1 |
| 5 | H | 1.60000 | 180.00000 | 0.00000 | 4 | 3 | 2 |
| 6 | H | 0.70000 | 180.00000 | 0.00000 | 5 | 4 | 3 |
| 7 | H | 1.60000 | 180.00000 | 0.00000 | 6 | 5 | 4 |
| 8 | H | 0.70000 | 180.00000 | 0.00000 | 7 | 6 | 5 |
| 9 | H | 1.60000 | 180.00000 | 0.00000 | 8 | 7 | 6 |
| 10 | H | 0.70000 | 180.00000 | 0.00000 | 9 | 8 | 7 |
| 11 | H | 1.60000 | 180.00000 | 0.00000 | 10 | 9 | 8 |
| 12 | H | 0.70000 | 180.00000 | 0.00000 | 11 | 10 | 9 |

FIG. 20

| ATOM NO. | TYPE | CHARGE | ATOM ELECTRON DENSITY |
|---|---|---|---|
| 1 | H | -0.005996 | 1.0060 |
| 2 | H | 0.005921 | 0.9941 |
| 3 | H | -0.000363 | 1.0004 |
| 4 | H | 0.000427 | 0.9996 |
| 5 | H | -0.000065 | 1.0001 |
| 6 | H | 0.000075 | 0.9999 |
| 7 | H | 0.000075 | 0.9999 |
| 8 | H | -0.000065 | 1.0001 |
| 9 | H | 0.000427 | 0.9996 |
| 10 | H | -0.000363 | 1.0004 |
| 11 | H | 0.005921 | 0.9941 |
| 12 | H | -0.005996 | 1.0060 |

FIG. 21

| NO. | ATOM | X | Y | Z |
|---|---|---|---|---|
| 1 | H | 0.0000 | 0.0000 | 0.0000 |
| 2 | H | 0.7000 | 0.0000 | 0.0000 |
| 3 | H | 2.3000 | 0.0000 | 0.0000 |
| 4 | H | 3.0000 | 0.0000 | 0.0000 |
| 5 | H | 4.6000 | 0.0000 | 0.0000 |
| 6 | H | 5.3000 | 0.0000 | 0.0000 |
| 7 | H | 6.9000 | 0.0000 | 0.0000 |
| 8 | H | 7.6000 | 0.0000 | 0.0000 |
| 9 | H | 9.2000 | 0.0000 | 0.0000 |
| 10 | H | 9.9000 | 0.0000 | 0.0000 |
| 11 | H | 11.5000 | 0.0000 | 0.0000 |
| 12 | H | 12.2000 | 0.0000 | 0.0000 |

METHOD AND APPARATUS FOR ANALYZING CHEMICAL SYSTEMS

BACKGROUND OF THE INVENTION

1. Field of the Invention

The present invention relates to a method and apparatus for analyzing chemical systems. More particularly, the present invention relates to a method and apparatus for analyzing large molecules using approximate molecular geometry.

2. Description of the Related Art

In classical mechanics, it is assumed that particles can possess arbitrary amounts of energy. However, on a molecular scale, this assumption fails. Therefore, quantum mechanics was developed to predict the amount of energy possessed by a particle and the probability that a particle will be positioned at a certain point. Quantum mechanics are explained in detail in texts such as *Physical Chemistry*, which is hereby incorporated by reference in its entirety for all purposes.

Quantum mechanics can be used to study chemical compounds and ions which are molecules which have acquired a charge due to the gain or loss of electron(s). Hereinafter, the terms "chemical system" and "chemical compound" are used synonymously to encompass chemical compounds and ions.

As part of the quantum mechanical analysis, it is necessary to solve Schrödinger's equation which is represented as:

$$H\psi = E\psi$$

where H is the Hamiltonian operator which is a grouping of parameters for the particular chemical system; $\psi$ is the wave function (an operator) which replaces the classical concept of trajectory; and E is the energy of the particle.

According to the Born approximation, the probability density of a particle (the probability that a particle will occupy a certain position) is given by the square of the wavefunction, $\psi^2$.

In a many electron system, an analytical solution is impossible. However, very powerful computational techniques are available to provide detailed and reliable numerical solutions for the wavefunctions and the energies.

A solution to Schrödinger's equation allows one to optimize molecular structure by minimizing the energy of the particles. There are at least two computational techniques to determine molecular structure including the semi-empirical methods, which combine empirical data and quantum mechanical calculations, and ab initio methods, which involve calculation of orbital integrals based on first principles.

An example of a semi-empirical method is AM1, PM3, and MNDO which are found in MOPAC 93 (Molecular Orbital PACkage). To understand the MOPAC 93 method, it is helpful to look at an example. The exact calculations of this example are described on pages 118–123 of the MOPAC 93 Manual, which is hereby incorporated by reference in its entirety for all purposes. The steps which are described below are shown in the flow chart of FIG. 1.

The system to be examined is a regular hexagon of hydrogen atoms in which the H—H distance is 0.98316. Of course, a regular hexagon of hydrogen atoms is not a stable system; the only reason it is being used is to demonstrate the working of a self consistent field ("SCF") calculation.

In the analysis, first an approximate atomic distance is input (step 1 in FIG. 1) which is converted to an interatomic distance matrix, shown below, where the distance is given in Angstroms.

| Atom | Interatomic Distance Matrix (Å) | | | | | |
|---|---|---|---|---|---|---|
| | 1 | 2 | 3 | 4 | 5 | 6 |
| 1 | 0.0000 | | | | | |
| 2 | 0.9832 | 0.0000 | | | | |
| 3 | 1.7029 | 0.9832 | 0.0000 | | | |
| 4 | 1.9663 | 1.7029 | 0.9832 | 0.0000 | | |
| 5 | 1.7029 | 1.9663 | 1.7029 | 0.9832 | 0.0000 | |
| 6 | 0.9832 | 1.7029 | 1.9663 | 1.7029 | 0.9832 | 0.0000 |

Then, the interatomic distance matrix is used to determine a one-electron matrix (step 2 in FIG. 1) which ignores the effects of other electrons. The one-electron matrix is shown below:

| Atom | One-electron matrix (eV) | | | | | |
|---|---|---|---|---|---|---|
| | 1 | 2 | 3 | 4 | 5 | 6 |
| 1 | −51.7124 | | | | | |
| 2 | −3.2457 | −51.7124 | | | | |
| 3 | −1.0970 | −3.2457 | −51.7124 | | | |
| 4 | −0.6992 | −1.0970 | −3.2457 | −51.7124 | | |
| 5 | −1.0970 | −0.6992 | −1.0970 | −3.2457 | −51.7124 | |
| 6 | −3.2457 | −1.0970 | −0.6992 | −1.0970 | −3.2457 | −51.7124 |

In order to solve Schrödinger's equation it is necessary to determine the electron-electron interaction for each of the electrons of the molecule (in each molecular orbital). The potential energy of each electron depends upon the potential energy of every other electron. Thus, the potential energies are initially guessed and solving Schrödinger's equation is preformed iteratively. The cyclic calculations are performed until the orbitals and the energies obtained are insignificantly different from those used at the start of the latest cycle. The solutions are then said to be self-consistent, and accepted as solutions of the problem.

The analog of the one-electron matrix in Hückel theory is the Alphas and Betas. See section 16.4(a) of P. W. Atkins, *Physical Chemistry*, Third Edition (1986) for a discussion on Hückel's theory. The diagonals are the energy an electron would have if it were only on one atom (the wavefunction of one atom).

The off-diagonals are the energy the electron would have if it were in the wavefunction of two different atoms. As can be seen, as the distance between the atoms becomes greater (refer to the distance matrix), the energy of the electron becomes smaller (is inversely proportional to the distance).

This is because there is a larger interaction between close atoms.

Then, inter-electron interactions are considered. A calculation is made as to the energy a first electron would have if it were in the field of a second electron (step 3 in FIG. 1). The resulting two electron integrals are shown below, where the energy is given in electron volts:

|      | Two-Electron Integrals (eV) |         |         |         |        |         |
| Atom | 1       | 2       | 3       | 4       | 5       | 6       |
| --- | --- | --- | --- | --- | --- | --- |
| 1 | 12.8480 |         |         |         |         |         |
| 2 | 9.6585  | 12.8480 |         |         |         |         |
| 3 | 7.0635  | 9.6585  | 12.8480 |         |         |         |
| 4 | 6.3622  | 7.0732  | 9.6585  | 12.8480 |         |         |
| 5 | 7.0635  | 6.3622  | 7.0732  | 9.6585  | 12.8480 |         |
| 6 | 9.6585  | 7.0635  | 6.3622  | 7.0732  | 9.6585  | 12.8480 |

The energy is positive because the electrons are repelling one another.

A density matrix is necessary in order to calculate the Fock matrix, but, in turn, the Fock matrix is necessary in order to calculate the density matrix. To break this impasse, a guessed density matrix is formed (step 4 in FIG. 1). The guess is very crude: all off-diagonal matrix elements are set to zero, and all on diagonal terms on any atom are set equal to the core charge of that atom divided by the number of atomic orbitals. In other words, all electrons are assumed to be localized on their respective atoms. Our starting guess for $H_6$ consists of a unit matrix (1's on the diagonals). The starting density matrix is not shown.

Each iteration of the SCF calculation consists of assembling a Fock matrix from the one-electron matrix, the two-electron integrals, and the density matrix, diagonalizing it to obtain the eigenvectors, and finally reassembling the density matrix. At some point the change in the density matrix drops below a preset limit. When this happens we say that the field is self-consistent. These steps will now be carried out for the $H_6$ system.

Formation of the initial Fock matrix (step 5 in FIG. 1) is simple, as there are no off-diagonal terms in the density matrix. Therefore the off-diagonal terms for the initial Fock matrix are the same as those terms in the one-electron matrix.

The on-diagonal terms in the initial Fock matrix Faa are modified by the electrostatic field of all the electrons in the system except the electron or fraction of an electron in the atomic orbital $\phi_a$. Consider F(1,1). The total initial population of $\phi_1$ is 1.0 (from the starting density matrix), composed of equal amounts of $\alpha$ and $\beta$ electron density. An electron in $\phi_1$ would therefore experience the electrostatic repulsion of half an electron. An electron cannot repel itself; however, it will be repelled by its partner electron of opposite spin.

In addition, each electron will be affected, normally repelled, by the electrostatic field of all the electrons on all the other atoms. Each atom has one electron, so the total energy of an electron, i.e., the diagonal initial Fock matrix element, is given by:

$$F(1,1) = -51.7124 + \tfrac{1}{2}(12.848) + 2(9.6585 + 7.0635) + 6.3622.$$

The initial Fock matrix is obtained by adding the two-electron terms to the one-electron matrix. The elements of the initial Fock matrix represent the sum of the one and two electron interactions. For the system of six hydrogen atoms, this has the following form:

|      | Initial Fock Matrix (eV) |         |         |         |         |         |
| Atom | 1       | 2       | 3       | 4       | 5       | 6       |
| --- | --- | --- | --- | --- | --- | --- |
| 1 | −5.4823 |         |         |         |         |         |
| 2 | −3.2457 | −5.4823 |         |         |         |         |
| 3 | −1.0970 | −3.2457 | −5.4823 |         |         |         |
| 4 | −0.6992 | −1.0970 | −3.2457 | −5.4823 |         |         |
| 5 | −1.0970 | −0.6992 | −1.0970 | −3.2457 | −5.4823 |         |
| 6 | −3.2457 | −1.0970 | −6.6992 | −1.0970 | −3.2457 | −5.4823 |

The initial Fock matrix is then diagonalized (step 6 in FIG. 1) to yield the following set of eigenvalues, or one-electron energies, and eigenvectors, or molecular orbitals. The energy levels listed to the left represent the molecular orbitals. Because the example is directed to an $H_6$ system, only 6 electrons are present and only the lowest three energy levels are occupied. To the left of the energy levels are the molecular orbital ("MO") coefficients.

|               | Molecular Orbital Coefficients |         |         |         |         |         |
| Energy Level  | 1      | 2       | 3       | 4       | 5       | 6       |
| --- | --- | --- | --- | --- | --- | --- |
| 6 −0.4857   | 0.4082 | −0.4082 | 0.4082  | −0.4082 | 0.4082  | −0.4082 |
| 5 −1.8388   | 0.5774 | −0.2887 | −0.2887 | 0.5774  | −0.2887 | −0.2887 |
| 4 −1.8388   | 0.0000 | 0.5000  | −0.5000 | 0.0000  | 0.5000  | −0.5000 |
| 3 −6.9317   | 0.5774 | 0.2887  | −0.2887 | −0.5774 | −0.2887 | 0.2887  |
| 2 −6.9317   | 0.0000 | 0.5000  | 0.5000  | 0.0000  | −0.5000 | −0.5000 |
| 1 −14.8670  | 0.4082 | 0.4082  | 0.4082  | 0.4082  | 0.4082  | 0.4082  |

A new density matrix, shown below, is then calculated (step 7 in FIG. 1) from the diagonalized Fock matrix:

| Atom | Density Matrix (eV) | | | | | |
|---|---|---|---|---|---|---|
| | 1 | 2 | 3 | 4 | 5 | 6 |
| 1 | 1.0000 | | | | | |
| 2 | 0.6667 | 1.0000 | | | | |
| 3 | 0.0000 | 0.6667 | 1.0000 | | | |
| 4 | −0.3333 | 0.0000 | 0.6667 | 1.0000 | | |
| 5 | 0.0000 | −0.3333 | 0.0000 | 0.6667 | 1.0000 | |
| 6 | 0.6667 | 0.0000 | −0.3333 | 0.0000 | 0.6667 | 1.0000 |

The diagonal terms of the new density matrix are the sum of the squares of the MO coefficients for the first three energy levels times two. For example, the 1—1 one diagonal of the new density matrix is the MO 1 coefficient for energy level 1, 0.4082, squared, plus the MO 1 coefficient for energy level 2, 0.0000, squared, plus the MO 1 coefficient for energy level 3, 0.5774, squared. The sum of these three terms is then multiplied by two, because the spins of the electrons are in opposite directions.

The off-diagonal terms are determined in the same manner except the two different MO coefficients are multiplied, rather than squaring one MO coefficient. For example, the atom 1-2 term is determined by multiplying MO coefficients 1 and 2 in energy level one, multiplying MO coefficients 1 and 2 for energy level 2 and multiplying MO coefficients 1 and 2 for energy level three. Then these three products are added together and the sum is doubled.

A new Fock matrix can then be constructed (step 8 in FIG. 1) using the new density matrix. Each element of the new Fock matrix (below) is calculated by taking a corresponding term from the one-electron matrix and subtracting from it one half the product of the corresponding density matrix term and the corresponding two electron integral term.

| Atom | Second Fock Matrix (eV) | | | | | |
|---|---|---|---|---|---|---|
| | 1 | 2 | 3 | 4 | 5 | 6 |
| 1 | −5.4823 | | | | | |
| 2 | −6.4652 | −5.4823 | | | | |
| 3 | −1.0970 | −6.4652 | −5.4823 | | | |
| 4 | +0.3611 | −1.0970 | −6.4652 | −5.4823 | | |
| 5 | −1.0970 | +0.3611 | −1.0970 | −6.4652 | −5.4823 | |
| 6 | −6.4652 | −1.0970 | +0.3611 | −1.0970 | −6.4652 | −5.4823 |

Because the on-diagonal terms of the new density matrix are one, the on-diagonal terms of the new Fock matrix are identical to those in the initial Fock matrix. The off-diagonal terms are however changed. The off-diagonal terms are modified to allow for exchange interactions. (Note that not all exchange terms are stabilizing.)

The new Fock matrix element F(1,2), for example, is evaluated as follows:

$$f(1,2) = -3.2457 - \tfrac{1}{2}(0.6667)(9.6583) \ eV$$

Next, it is determined if there is self consistency (step 9 in FIG. 1). This is done by diagonalization of the new Fock matrix and comparing the total electron energy of the resulting matrix with the matrix originally obtained. Alternatively, the new density matrix could be used to determine if there is self consistency. Other elements of the analysis could also be used. In this case the same set of eigenvectors are obtained as were initially obtained (the eigenvalues obviously will be different). Thus, because there is no change, the comparison has shown that the difference is below a preset threshold and there is self-consistency, and the SCF calculation is complete (10 in FIG. 1). This is quite unusual and the simplicity is one reason the $H_6$ hexagonal system was chosen. In general, several iterations are necessary in order to obtain an SCF. If there is not self consistency, the Fock matrix is diagonalized (step 6 in FIG. 1) and the steps subsequent thereto are repeated.

Currently quantum chemical analysis on large chemical systems such as enzymes is impractical even with the fastest semi-empirical methods such as MOPAC 93 and ab initio methods, such as GAUSSIAN, ATMOL, GRADSET, GAMES and HONDO. However, MOPAC 93 and all other semi-empirical and ab initio methods involve diagonalization of the Fock matrix. The computation time of diagonalization rises by the cube of the size of the matrix (number of atoms in the molecule). Even on the fastest supercomputer large molecules, such as enzymes, would require many years to process. Mathematicians have tried for many years to quicken the diagonalization step calculations. However, the analysis time for the diagonalization step still rises as the third power as the size of the Fock matrix.

SUMMARY OF THE INVENTION

An object of the present invention is to provide a method and apparatus for analyzing chemical systems which is faster than those of the related art.

It is a further object of the present invention to provide a method and apparatus for analyzing chemical systems in which the step of diagonalization of the Fock matrix is not required.

According to the present invention a method and apparatus is provided in which localized molecular orbitals are formed which are used to form a density matrix and a Fock matrix. An annihilation is then performed to iteratively eliminate the interaction of all bonding with all non-bonding orbitals. The annihilation process involves a simple diagonalization of a 2×2 matrix and replaces the very lengthy calculation of diagonalizing the Fock matrix, as was done in the related art. To further speed up the process, the method and apparatus of the present invention involve determining which of the bonding orbitals and antibonding orbitals cannot interact. This is done using interatomic distances. According to the present invention the analysis time increases approximately linearly with the number of atoms in the molecule, not as the cube of the number of atoms, as was the case with the related art.

The above-mentioned and other objects and features of the present invention will become more apparent from the following description when read in conjunction with the accompanying drawings. However, the drawings and descriptions are merely illustrative in nature and not restrictive.

BRIEF DESCRIPTION OF THE DRAWINGS

FIG. 5 is a table illustrating a data file of a geometry of a $H_{12}$ molecule;

FIG. 6 is a table of the Cartesian coordinates of the molecule $H_{12}$;

FIGS. 7A and 7B are a table of the one-electron matrix of the $H_{12}$ molecule;

FIG. 8 is a table of two-electron integrals of the $H_{12}$ molecule;

FIG. 9 is a table of the starting localized molecular orbitals of the $H_{12}$ molecule;

FIGS. 10A and 10B are a table of the density matrix of the $H_{12}$ molecule;

FIGS. 11A and 11B are a table of the Fock matrix of the $H_{12}$ molecule;

FIG. 12 is a table of localized molecular orbitals of the $H_{12}$ molecule resulting from annihilation of the first iteration;

FIGS. 13A and 13B are a table of the density matrix of the $H_{12}$ molecule of the first iteration;

FIGS. 14A and 14B are a table of the Fock matrix of the $H_{12}$ molecule of the first iteration;

FIGS. 15A and 15B are a table of the density matrix of the eleventh iteration;

FIGS. 16A and 16B are a table of the Fock matrix of the eleventh iteration;

FIG. 17 is a table illustrating the localized MOs after the eleventh iteration;

FIG. 18 is a table providing the heat of formation after the eleventh iteration;

FIG. 19 is a table of the molecular geometry after the eleventh iteration;

FIG. 20 is a table of atomic charges and dipole contributions of the $H_{12}$ molecule;

FIG. 21 is a table of the Cartesian coordinates of the $H_{12}$ molecule.

DETAILED DESCRIPTION OF THE PREFERRED EMBODIMENTS

Figure 1:
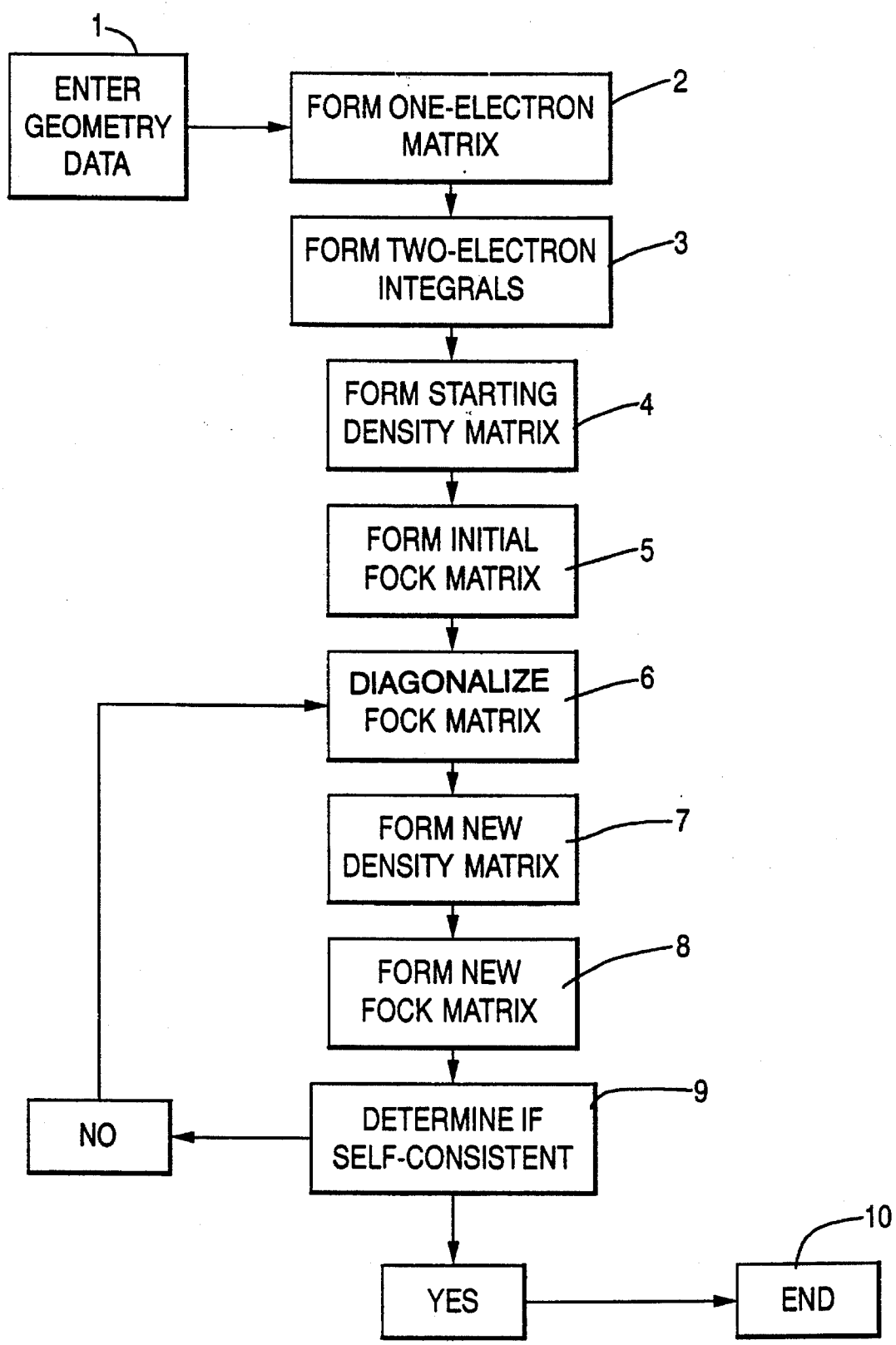
FIG. 1 is a flowchart for describing the method and apparatus of the related art.
Figure 2:
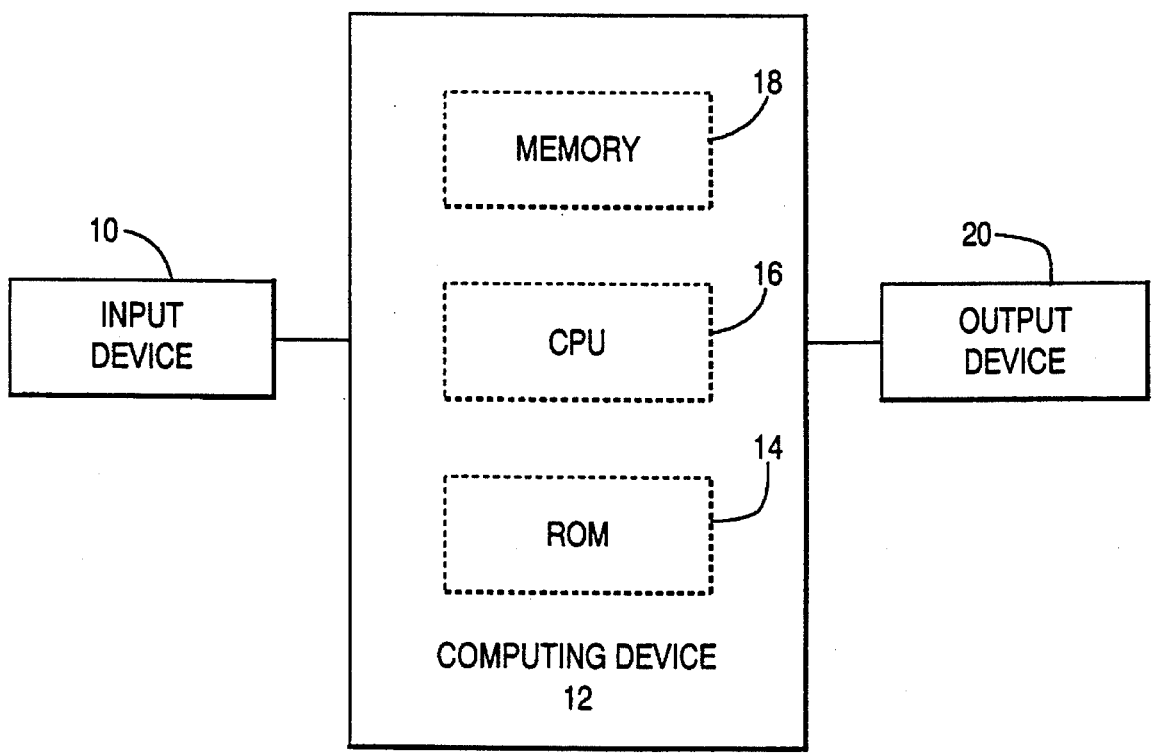
FIG. 2 is a diagram illustrating one embodiment of the present invention.

The present invention involves a quantum chemical analysis on large chemical systems and implements a new way of solving the self consistent field equations. FIG. 2 illustrates one embodiment implementing the present invention. The apparatus comprises an input device 10 for inputting data to a computing device 12. The computing device 12 comprises a ROM 14, a central processing unit (CPU) 16 and a memory 18. The computing device 12 may comprise more than one CPU. The computing device 12 performs the chemical analysis of the data provided by the input device. The computing device 12 also transmits results of the analysis to an output device 20 such as a CRT (cathode ray tube) or a printer. Several output devices may be connected to computing device 12 for receiving the results of the chemical analysis. Control words including key words on pages 14–17 of the MOPAC 93 manual are used to control the analysis and output of the results. The apparatus which would best implement this quantum chemical analysis includes a super computer such as one manufactured by Cray or Fujitsu Limited. However, computers having 132 megabytes of memory such as a Sun Sparc 2 may be used to perform the analysis on less complex chemical systems in a timely fashion.

The present invention replaces the present subroutine ITER in the semi-empirical analysis of MOPAC 93 with a new subroutine having the same name. The complete analysis is described in Fortran code which was submitted on microfiche concurrently with the present application and is on reserve with the U.S. Patent and Trademark Office and which is hereby incorporated by reference in its entirety for all purposes. With the new subroutine ITER the time consuming diagonalization of the Fock matrix of the MOPAC 93 is unnecessary. The subroutine ITER referred to throughout the remainder of the application refers to subroutine ITER of the present invention.

Figure 3A:
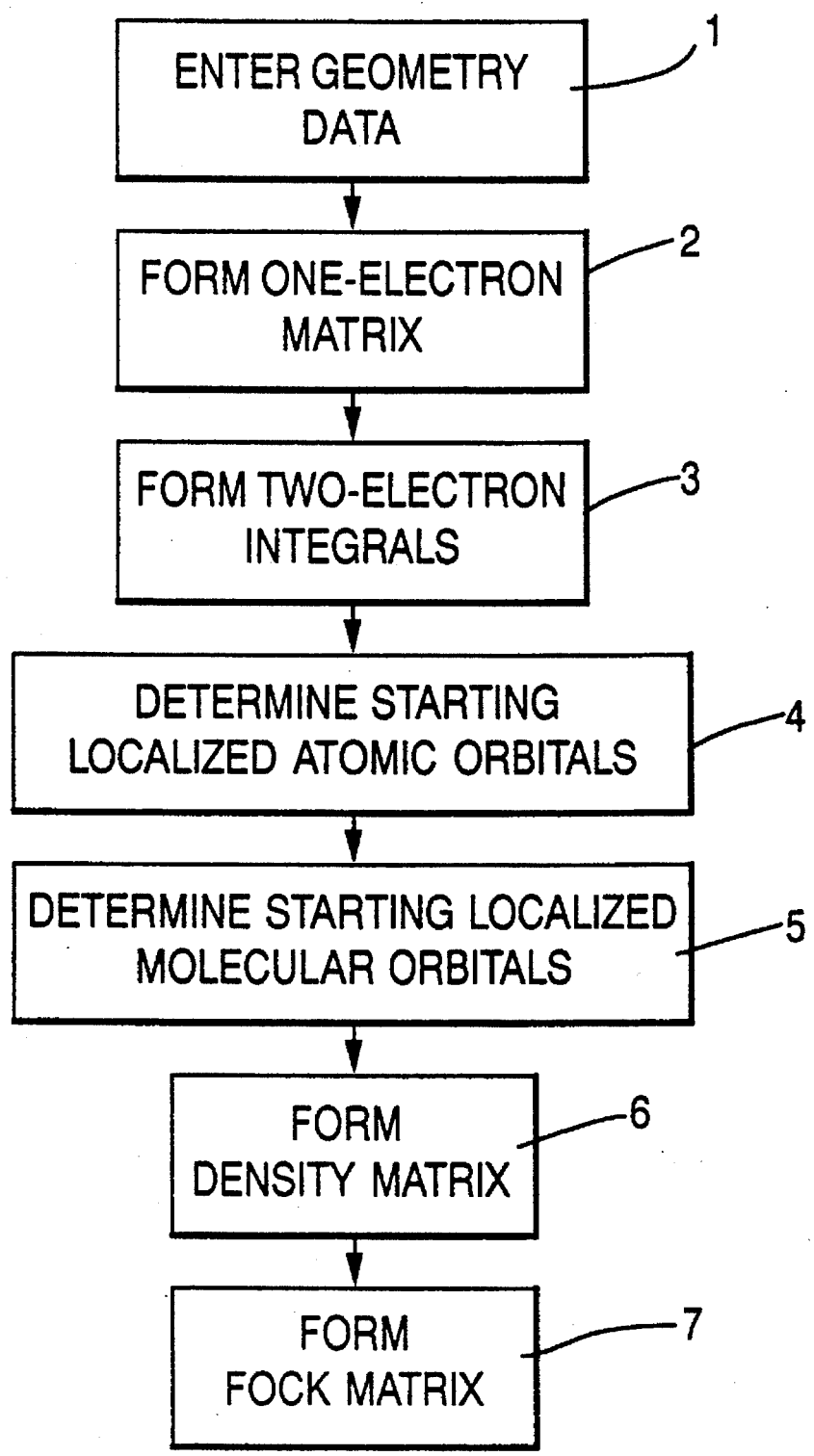
FIGS. 3A and 3B are first and second portions, respectively of a flowchart for describing the method and apparatus of the present invention.
Figure 3B:
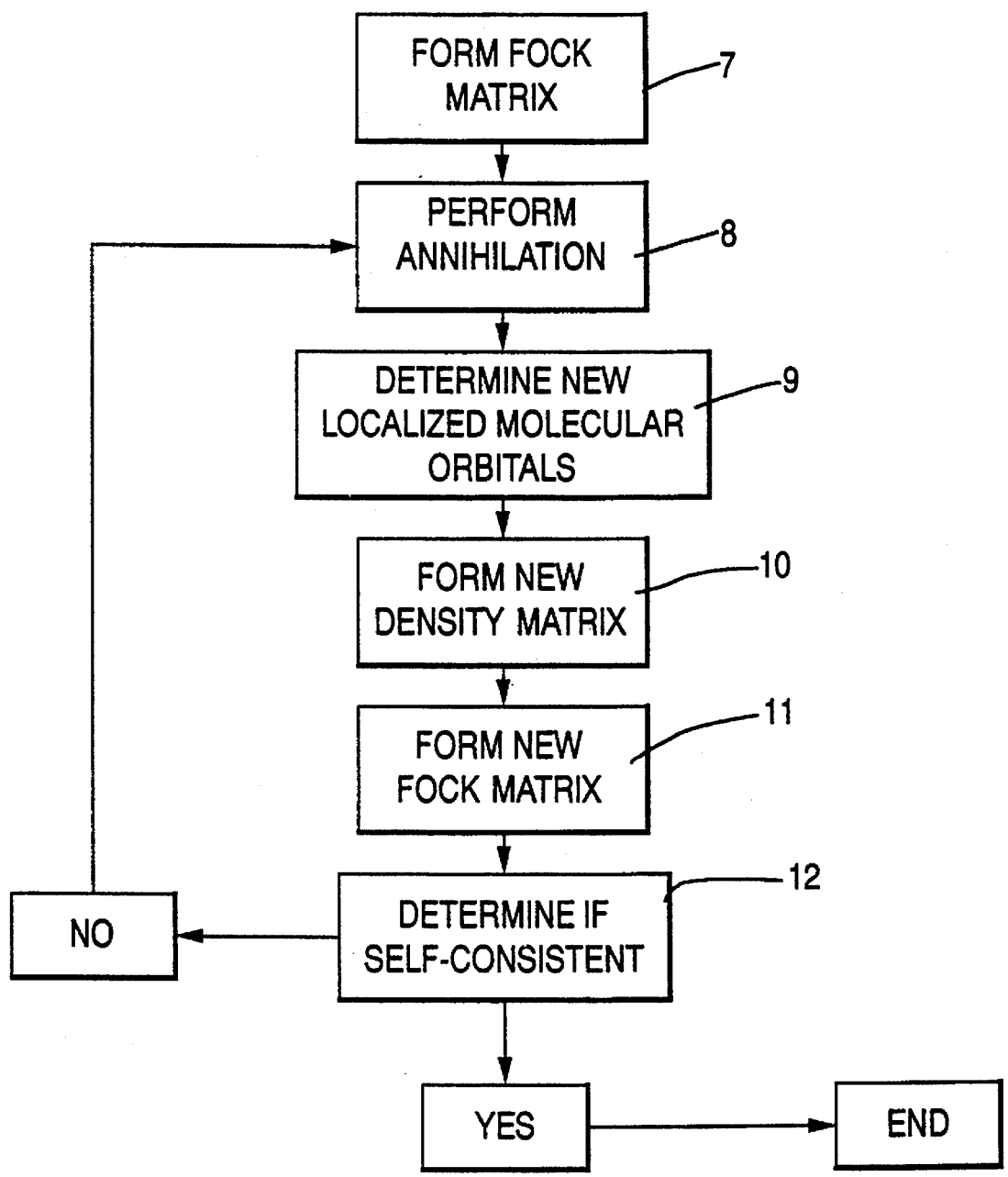

FIGS. 3A and 3B are first and second portions, respectively of a flowchart for describing the method and apparatus of the present invention. In order to begin the analysis, an operator generates a data file or utilizes an already existing data file, which represents the approximate molecular geometry of a chemical system such as an enzyme (step 1 in FIG. 3A). From the data file, the Cartesian coordinates indicative of the molecular geometry of the chemical system are determined using a method well known in the art.

A one-electron matrix is then formed in the same manner as was done in MOPAC 93 (step 2 in FIG. 3A).

Two-electron integrals for each atom in the molecule are also formed (step 3 in FIG. 3A). The two electron integrals are calculated from molecular geometry of the data file using the same methods as those described for MOPAC 93.

Since the diagonalization of the Fock matrix is very time consuming, a new analysis, which is found in subroutine MAKVEC and called by ITER, is utilized to provide localized molecular orbitals (LMOs). The localized molecular orbitals are used to provide a new density matrix (to be described later). The starting localized molecular orbitals are determined from starting localized atomic orbitals (step 4 in FIG. 3A).

To form the starting localized atomic orbitals, the chemical structure is first determined. This is done with the entries in the one-electron matrix which become vanishingly small as the atoms are located further apart. Using known bonding characteristics of the elements and the distance between the electrons, the chemical structure is thus determined.

For each non-hydrogen atom, all the chemically-bonded neighbors are then identified using MAKVEC and HYBRID. For example, the analysis begins with atom A. The energy terms representing the interaction of the atom A with the S atomic orbital of atom A's neighbors is put into a small secular determinant. The size of the secular determinant is four plus the number of neighbors. The energy terms for the atom A with itself are all set to zero. The energy terms for all other iterations are also set to zero. Diagonalization of the secular determinant yields diatomic molecular orbitals. The number of diatomic molecular orbitals is equal to the number of neighbors. Localization of these diatomic MO's yields hybrid atomic orbitals on atom A.

Then, using the starting localized atomic functions (localized atomic orbitals), starting localized molecular orbitals (LMOs) are formed (step 5 in FIG. 3A). The starting LMOs will be either monoatomic or diatomic. As a localized bond is formed, a localized anti-bond is also formed. The steps in determining the starting LMOs are as follows:

First, for each atom, in turn, the number of atoms bonded to it are identified. Localized molecular diatomic bonding and antibonding orbitals for the a framework are formed by MAKVEC. A count is kept for how many of the atomic orbitals are used in the σ framework. Because hydrogen has only a G bond, the localized atomic orbital will be the same as the localized molecular orbital for hydrogen. For all other atoms, a subroutine HYBRID determines the SP hybrids to produce localized molecular orbitals corresponding to all the atoms in the chemical system. The analysis in HYBRIB is performed in the second through fifth steps.

Second, for each atom in turn, the lone pairs (monoatomic hybrids) are identified and formed by MAKVEC.

Third, for each atom in turn, the localized ρ bonds are identified and are formed by MAKVEC.

Fourth, for each atom in turn, the delocalized ρ bonds are identified and formed by MAKVEC.

Fifth, for each atom in turn, any remaining ρ bonds are identified and formed by MAKVEC.

A density matrix is then calculated as shown in step 6 of FIG. 3A. The density matrix is formed in a manner similar to that of the related art (MOPAC 93). For every occupied localized molecular orbital, the squared entry is added to the other entry, which also has been squared, and multiplied by two.

A Fock matrix is generated based on a one-electron matrix, the two-electron integrals and the density matrix in the same manner as in the related art. This is step 7, which is shown in both FIGS. 3A and 3B.

Then, using the starting localized molecular orbitals, annihilation takes place (step 8 in FIG. 3B). This is done in DIAGG. DIAGG replaces the diagonalization of the Fock matrix step of the related art. The name is the same as that of the related art to indicate the similarity. The annihilation is basically diagonalizing the following 2×2 matrix (2×2 rotation):

$$\begin{vmatrix} <\psi_i F \psi_i> & <\psi_i F \psi_j^*> \\ <\psi_i F \psi_j^*> & <\psi_j^* F \psi_j^*> \end{vmatrix}$$

where $\psi_i$ is the molecular orbital i and $\psi_j^*$ is the coefficient for the antibonding molecular orbital j. The above 2×2 diagonalization is done for every possible interaction of a bonding orbital with an antibonding orbital in order to reduce each interaction to zero. Note that the annihilation process does not consider bonding-bonding interactions and also does not consider antibonding-antibonding interactions.

Diagonalizing a 2×2 matrix is very simple and only involves taking the square root. (Recall the complex math discussed with regard to diagonalizing large Fock matrices in the analysis of the related art.) Diagonalization will yield a new $\psi_i$ equivalent to $Cos(\theta \psi_i) + Sin(\theta \psi_j^*)$. The new $\psi_j^*$ is equivalent to $-Sin(\theta \psi_i) + Cos(\theta \psi_j^*)$.

In doing an annihilation, the numbers are perturbed for each of the previously annihilated bonding and antibonding molecular orbitals. Therefore, although the mixing of a particular bonding orbital and a particular non-bonding orbital sets the interaction to zero, during the next annihilation, the energy becomes non-zero.

As stated above, every integral representing the interaction of a bonding orbital and an antibonding orbital eventually becomes zero (self-consistency). In this manner, the energy of each bonding molecular orbital is minimized to form a stable system with regard to the antibonding MO and the bonding MO being considered.

The result of the annihilation step is formation of new localized molecular orbitals (step 9 in FIG. 3B).

During the first annihilation, a check is made in MAKVEC to see if the occupied LMO (bonding) and the virtual MOs (antibonding) have any atoms in common (orbital overlap). This is accomplished based on whether the interatomic distance between the atoms is less than a preset cutoff. Preferably, the preset cutoff is 12 Angstroms. In doing this operation, if $\psi_i$ and $\psi_i^*$ are more than 12 Angstroms away from one another, the interaction is not considered. In a carbon chain, elimination begins to occur at about $C_{20}$. However, because of other complexities associated with the procedure, an increase in speed cannot be seen until about a $C_{100}$ molecule and the procedure can easily be used on a molecule having greater than 200 atoms.

A new density and a new Fock matrix are formed in steps 10 and 11, respectively, as shown in FIG. 3B. The new density matrix and new Fock matrix are respectively formed in the same manner as steps 6 and 7 of FIG. 3A.

Then, the subroutine ISITSC checks to see if the field is self-consistent (step 12 in FIG. 3B). This subroutine determines if there is self consistency by comparing the heat of formation after annihilation with that before annihilation. In determining the heat of formation a conversion is made to convert the energy from electron volts to kCal. SCFCRI is the self consistent field criteria. It is preset limit to determine how precise the calculation should be. When the heat of formation does not change within the preset limit (SCFCRI), the field is self consistent. In essence, what is being done is the new density matrix is being compared with the previous density matrix.

If the field is self consistent, the analysis is complete. If the field is not self consistent, step 8 and the subsequent steps are repeated, as shown in FIG. 3B. It should be noted that the invention is not limited to the use of the density matrix and heat of formation in determining whether the field is self consistent.

After a predetermined number of iterations, a subroutine LOCAL is called after the annihilation step. As the iterations proceed, the LMOs tend to spread out. Function LOCAL restrains the LMOs. This subroutine is found in the related art and is referred to as the Perkins—Stewart routine in the MOPAC 93 manual.

In the usual course of analysis, the geometry of the molecule is changed automatically after each SCF calculation has been completed. In this manner, an optimum geometry can be obtained.

Near the beginning of all SCF calculations after the first SCF calculation, a check is made in a TIDY subroutine to see if any of the LMOs are vanishingly small. If the contributions of one or more atoms to an LMO are vanishingly small, a flag is set so that the annihilation will not be performed with regard to these orbitals.

As with the related art this information can be used to optimize the molecular geometry. Like the related art, this is done by automatically and repeatedly changing the predicted molecular geometry each time after a self consistent field is achieved.

Figure 4:
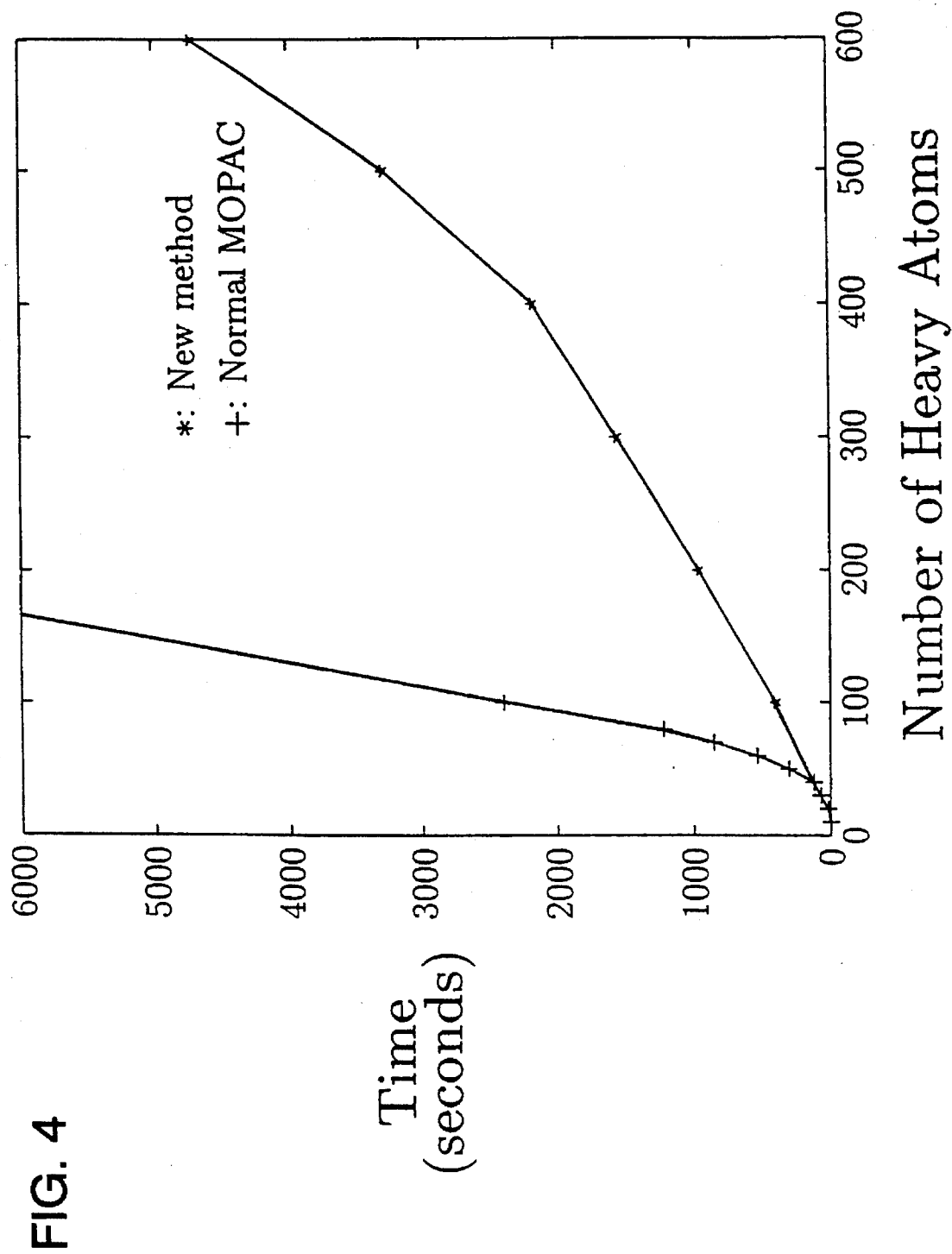
FIG. 4 is a diagram for explaining the increased speed in the analysis of the present invention.

The present method of the present invention avoids the need for diagonalizing a Fock matrix. As the size of the molecule being analyzed by the present invention increases, the time of the analysis increases approximately linearly, not with the cube of the size, as did the analysis of the related art. This quickening is illustrated in FIG. 4 by a plot of the time required for one SCF calculation versus the number of atoms in the molecule. In FIG. 4, the line formed by "+" entries represents those SCF calculations performed using the analysis of the related art. The line formed by "*" entries represents those SCF calculations performed using the analysis of the present invention. Clearly, a significant reduction in analysis time is achieved. Whereas before it was impossible to analyze large molecules, even those with only a few hundred atoms, very large molecules including enzymes can be now analyzed according to the present invention.

EXAMPLE 1

Example 1 is directed to the analysis of an $H_{12}$ molecule. Although an $H_{12}$ molecule is small and maybe unstable, the example illustrates the steps in the analysis except for producing hybrid orbitals. This analysis will not produce hybrid orbitals because hydrogen only has an S valence shell.

FIG. 5 is a table showing the geometric configuration of the $H_{12}$ molecule. The first column is for the atom number and the hydrogen atoms 1–12 are shown. The second column is the atomic symbol. The third column is the bond length in Angstroms. The bond length is approximated to be 0.7 angstroms. The 1.6 entries in the third column is the distance from the previous atom with which the 3, 5, 7, etc. atoms are not bonding. Since the first atom does not bond with itself, no bond length is given. The fourth column is the angle of the bond of that atom with the bond of the previous atoms. The fifth column is a twist angle which is the angle of the bond having a plane formed by the previous three atoms. It follows that the twist angle is not given until the fourth atom.

As in the prior art, Cartesian coordinates based on the geometry of the $H_{12}$ molecule of FIG. 5 are determined as shown in FIG. 6.

Also as in the prior art, the one-electron matrix is determined from the geometry of the $H_{12}$ molecule of FIG. 5 and is shown in FIGS. 7A and 7B.

Further, two-electron integrals are generated based on the molecular geometry of FIG. 5 and are shown in FIG. 8.

Since hydrogen only has an S atomic orbital, hydrogen does not have hybrid orbitals. Therefore, no hybrid orbitals are generated. The atomic orbital of hydrogen is the same as the molecular orbital of hydrogen. The localized molecular orbitals are determine based on the molecular geometry of the molecule and are shown in FIG. 9. The first row and first two columns indicate the probability of two hydrogen atoms, hydrogen atom 1 and hydrogen atom 2 having the first two electrons. The second row and first two columns indicate the probability of the two electrons being associated with hydrogen atoms 3 and 4. The localized molecular orbitals are arranged in this fashion to save memory space.

FIGS. 10A and 10B shows the initial density matrix, which is determined from the localized molecular orbital by squaring the two LMO entries and adding them together.

FIGS. 11A and 11B are a table showing the Fock matrix derived from the one-electron matrix, two-electron integrals and the electron density matrix by the same method described with regard to the related art.

After the initial Fock matrix is generated, the first iteration begins. The initial localized MOs of FIG. 5 are now replaced with new localized molecular orbitals based on an annihilation of each bond with each antibond. For the $H_{12}$ system in which there are 6 orbitals (2 electrons per orbital), there are 36 annihilations. Each annihilation diagonalizes a 2×2 matrix. For example, to annihilate the interaction of the first bonding orbital with the second antibonding orbital, the interaction matrix is diagonalized.

Recall that when eliminating the interaction between $\psi_i$ and $\psi_j^*$, the elements of the 2×2 matrix to be diagonalized are $\psi_i F \psi_i$, $\psi_i F \psi_j^*$, $\psi_j^* F \psi_j^*$, and $\psi_j^* F \psi_j^*$. For this $H_{12}$ molecule, the diagonalization term, $\psi_1 F \psi_1^*$, for example, is equivalent to $H_1FH_1 - H_1FH_2 + H_2FH_1 - H_2FH_2$, where F is the Fock matrix and H represents a hydrogen atom coefficient. The diagonalization term, $\psi_1 F \psi_2^*$, for example, is equivalent to $\frac{1}{2}(H_1FH_3 - H_1FH_4 + H_2FH_3 - H_2FH_4)$. This works out to be $\frac{1}{2}(0-0+-0.1-0)=-0.05$. Note that the interaction is not shown in the diagrams. As can be seen by comparing the localized molecular orbitals before and after annihilation, MO No. 1 was 0.7071 on atoms 1 and 2 and zero on all other atoms. After annihilation, less energy is on atoms 1 and 2 and some of the energy is now on atoms 3 and 4.

During the first set of annihilations, a check is made to see if the occupied LMOs and the virtual MOs have any atoms in common. In this example, this is accomplished based on whether the interatomic distances between the atoms is less than a preset cutoff of 13 Angstroms. This eliminates elements which would be zero anyway and speeds up the program. The subroutine DIAGG which is called by the subroutine ITER performs the annihilation. The energy terms corresponding to the interaction of the bonding and antibonding LMOs are annihilated by mixing a portion of the non-bonding LMO with a portion of the bonding LMO and vice versa. After this is completed, a new set of LMOs results, as shown in FIG. 12. FIGS. 13A, 13B, 14A and 14B illustrate the density matrix and Fock matrix in iteration one, respectively. In this particular molecule, 11 iterations were necessary for the density matrix was self consistent. Each iteration involves annihilation, forming localized molecular orbitals, forming a new density matrix, formation of a Fock matrix and a check for self consistency.

In this example, at iteration 11 the largest change in the density matrix was less than a preset cutoff and the change in heat of formation was less than a preset cutoff. FIGS. 15A, 15B, 16A, 16B and 17 show the density matrix, the Fock matrix and the local molecular orbitals, respectively, all after iteration 11. FIGS. 18–21 illustrate the heat of formation, molecular geometry, atomic charges and dipole contribution, and Cartesian coordinates of $H_{12}$, respectively.

This information can be used to generate the following chemical properties concerning the $H_{12}$ molecule:

Excited States;
Geometry optimizations, etc., on specified states;
Single SCF calculation;
Geometry optimization;
Gradient minimization;
Transition state location;
Reaction path coordinate calculation;
Force constant calculation;
Normal coordinate analysis;
Transition dipole calculation;
Thermodynamic properties calculation;
Localized orbitals;
Solution-phase effects;
Covalent bond orders;

Bond analysis into σ and ρ contributions;

Dynamic Reaction Coordinate calculation;

Intrinsic Reaction Coordinate calculation.

While the invention has been illustrated and described in detail in the drawings and foregoing description, it will be recognized that many changes and modifications will occur to those skilled in the art. Therefore the appended claims are intended to cover any such changes and modifications which fall within the true spirit and scope of the invention.

I claim:

1. An apparatus for analyzing a chemical compound, comprising:

memory means for storing information on molecular geometry of a model of a model of the chemical compound, the chemical compound having an energy which converges;

processing means for:

forming localized molecular orbitals of the chemical compound based on the molecular geometry;

forming a Fock matrix for the chemical compound based on the localized molecular orbitals;

determining distances between bonding orbitals $\psi_i$ and non-bonding orbitals $\psi_j^*$;

eliminating an interaction between bonding orbitals $\psi_i$ and non-bonding orbitals $\psi_j^*$ only if the distance between the bonding orbital $\psi_i$, and the non-bonding orbital $\psi_j^*$ is less than a predetermined distance, using a corresponding member F of the Fock matrix by diagonalizing the following 2×2 matrix:

$$\begin{vmatrix} <\Psi_i F \Psi_i> & <\Psi_i F \Psi_j^*> \\ <\Psi_i F \Psi_j^*> & <\Psi_j^* F \Psi_j^*> \end{vmatrix}$$

determining if the energy of the chemical compound has converged within a preset limit; and repeating the formation of localized molecular orbitals, the formation of the Fock matrix and the elimination of the interaction between bonding orbitals $\psi_i$ and non-bonding orbitals $\psi_j^*$ if it is determined that the energy of the chemical compound has not converged within the preset limit; and output means for producing an output analysis of the chemical compound if the processing means determines that the energy of the chemical compound has converged within the preset limit.

2. An apparatus for analyzing a chemical compound, comprising:

memory means for storing information on molecular geometry of a model of the chemical compound, the chemical compound having an energy which converges;

processing means for:

forming localized molecular orbitals of the chemical compound based on the molecular geometry;

forming a Fock matrix for the chemical compound based on the localized molecular orbitals;

eliminating an interaction between bonding orbitals $\psi_i$ and non-bonding orbitals $\psi_j^*$ using a corresponding member F of the Fock matrix by diagonalizing the following 2×2 matrix:

$$\begin{vmatrix} <\Psi_i F \Psi_i> & <\Psi_i F \Psi_j^*> \\ <\Psi_i F \Psi_j^*> & <\Psi_j^* F \Psi_j^*> \end{vmatrix}$$

determining if the energy of the chemical compound has converged within a preset limit; and repeating the formation of localized molecular orbitals, the formation of the Fock matrix and the elimination of the interaction between bonding orbitals $\psi_i$ and non-bonding orbitals $\psi_j^*$ if it is determined that the energy of the chemical compound has not converged within the preset limit; and output means for producing an output analysis of the chemical compound if the processing means determines that the energy of the chemical compound has converged within the preset limit.

* * * * *

UNITED STATES PATENT AND TRADEMARK OFFICE
CERTIFICATE OF CORRECTION

PATENT NO. : 5,604,686

DATED : February 18, 1997

INVENTOR(S) : James J.P. STEWART

It is certified that error appears in the above-indentified patent and that said Letters Patent is hereby corrected as shown below:

<u>Col. 13</u>, line 14, delete the second occurrence of "of a model".

Signed and Sealed this

Fifteenth Day of July, 1997

Attest:

BRUCE LEHMAN

Attesting Officer     Commissioner of Patents and Trademarks